(12) United States Patent
Zhao

(10) Patent No.: US 7,811,555 B2
(45) Date of Patent: Oct. 12, 2010

(54) TRI-BRANCHED BIOLOGICALLY ACTIVE COPOLYMER

(75) Inventor: Jonathon Z. Zhao, Belle Mead, NJ (US)

(73) Assignee: Cordis Corporation, Bridgewater, NJ (US)

( * ) Notice: Subject to any disclaimer, the term of this patent is extended or adjusted under 35 U.S.C. 154(b) by 1236 days.

(21) Appl. No.: 11/323,274

(22) Filed: Dec. 30, 2005

(65) Prior Publication Data

US 2007/0154521 A1 Jul. 5, 2007

(51) Int. Cl.
*A61K 31/74* (2006.01)

(52) U.S. Cl. .................................... 424/78.1

(58) Field of Classification Search ........................ None
See application file for complete search history.

(56) References Cited

U.S. PATENT DOCUMENTS

| 4,973,493 | A | 11/1990 | Guire |
| 6,238,799 | B1 | 5/2001 | Opolski |
| 6,566,506 | B2 * | 5/2003 | Greenwald et al. ....... 530/391.1 |
| 2003/0113477 | A1 | 6/2003 | Timmons et al. |
| 2005/0266038 | A1 | 12/2005 | Glauser et al. |

FOREIGN PATENT DOCUMENTS

| WO | WO 03/059973 A2 | 7/2003 |
| WO | WO 03/078489 A1 | 9/2003 |

OTHER PUBLICATIONS

European Search Report dated Jun. 24, 2008 for EP Application No. EP 06256638.
Feng, Xiao-Shuang et al: "Synthesis of Amphiphilic Miktoarm ABC Star Copolymers by RAFT Mechanism Using Maleic Anhydride as Linking Agent" Macromolecules, vol. 35, No. 13, 2002, 4888-4893.
Shi, Peng-Jie et al., "Block and star block copolymers by mechanism transformation X . . . "European Polymer Journal, 2004, 20, 1283-1290.
www.surmodics.com.

* cited by examiner

*Primary Examiner*—Michael G Hartley
*Assistant Examiner*—James W Rogers

(57) ABSTRACT

The present invention discloses a tri-branched copolymer comprising a hydrophobic domain, a hydrophilic domain, a biologically active moiety, and an alkyl core of 2 to 10 carbon atoms. The hydrophobic domain, the hydrophilic domain, and the biologically active moiety are separately linked to the alkyl core of 2 to 10 carbon atoms through three functional groups, wherein said three functional groups are independently the same or different. Preferably, the tri-branched copolymer is prepared through reversible addition fragmentation transfer (RAFT) polymerization and conjugation reactions. The present invention also discloses a coating composition for applying on at least a portion of one surface of an article. The coating composition comprises the inventive tri-branched copolymer. In another aspect, the present invention discloses an article having the inventive coating composition thereon. Preferably, the article is a medical device or a component of a medical device.

6 Claims, No Drawings

TRI-BRANCHED BIOLOGICALLY ACTIVE COPOLYMER

FIELD OF THE INVENTION

The present invention relates to a tri-branched copolymer and a coating composition comprising the inventive copolymer for application to at least a portion of one surface of an article. The present invention also relates to an article having the inventive coating thereon.

BACKGROUND OF INVENTION

Most medical devices are made from metals, ceramics, or polymeric materials. However, these materials are hydrophobic, non-conformal, and non-slippery, and thereby may cause thrombus formation, inflammation, or other injuries to mucous membranes during use or operation. Thus, the issue of biocompatibility is a critical concern for manufacturers of medical devices, particularly medical implants. In order to function properly and safely, medical devices are usually coated with one or more layers of biocompatible materials. The coatings on these medical devices may, in some instances, be used to deliver therapeutic and pharmaceutical agents.

Since medical devices, particularly implantable medical devices, are intended for prolonged use and directly interface with body tissues, body fluids, electrolytes, proteins, enzymes, lipids, and other biological molecules, the coating materials for medical devices must meet stringent biological and physical requirements. These requirements, as a minimum, include the following: (1) the coatings must be hydrophilic and lubricous when in contact with body tissue, and thereby increase patient comfort during operation and enhance the maneuverability of the medical device; (2) the coatings must be flexible and elastic, so they conform to the biological structure without inducing detrimental stress; (3) the coatings must be hemocompatible, and thereby reduce or avoid formation of thrombus or emboli; (4) the coatings must be chemically inert to body tissue and body fluids; and (5) the coatings must be mechanically durable and not crack when formed on medical devices. If the coatings are impregnated with pharmaceutical or therapeutic agents, it is typically required that the coatings and the formation thereof are compatible with the pharmaceutical or therapeutic agents. If the coatings are used as coatings and the underlying basecoats are impregnated with pharmaceutical or therapeutic agents, it is further required that the coating and the formation thereof must be compatible with the basecoat and the pharmaceutical or therapeutic agents impregnated therein; and the coating must allow the pharmaceutical or therapeutic agents to permeate therethrough. It is also desirable that the coating functions as a physical barrier, a chemical barrier, or a combination thereof to control the elution of the pharmaceutical or therapeutic agents in the underlying basecoat.

In order to combine the desired properties of different polymeric materials, the conventional coating composition for commercial drug eluting stents used a polymer blend, i.e., physical mixture, of poly ethylene-vinyl acetate (EVAc) and poly butyl methacrylate (BMA). However, one disadvantage of this conventional coating is the phase separation of the polymer blend, which can be detrimental to the performance of the coating and the stability of drugs impregnated therein.

Another coating composition of the prior art comprises a supporting polymer and a hydrophilic polymer, wherein the supporting polymer contains functional moieties capable of undergoing crosslinking reactions and the hydrophilic polymer is associated with the supporting polymer (see, for example, U.S. Pat. No. 6,238,799). However, the preparation of this prior art coating composition employs chemical crosslinking reactions and a high temperature curing process, which are not compatible with a drug-containing coating.

The prior art also uses a coating composition formed by the gas phase or plasma polymerization of a gas comprising monomers of polyethylene glycol vinyl ether compounds (see, for example, U.S. Patent Application Publication 2003/0113477). However, the polymer prepared through the plasma process has poorly defined molecular weight and a large polydispersity. The plasma laid polymers of low molecular weight have limited mechanical durability. Further, plasma treatment can penetrate through the underlying basecoat and damage the drug content therein. Another problem with this prior art approach is that the free radicals or other high energy species generated in the plasma process may persist in the coating and cause drug content loss in the basecoat over time.

To decrease thrombosis caused by the use of medical devices, the prior art also modifies the coatings of medical devices via conjugating, i.e., covalently bonding, an antithrombotic agent (e.g., heparin) to the coatings (see, for example, U.S. Pat. No. 4,973,493 and www.surmodics.com). Although this approach may produce a coating with excellent antithrombotic property, the prior art conjugation methods employ complex preparation processes and produce various by-products that may cause degradation of the antithrombotic agent in the coating.

Thus, there remains a need for a polymeric material and a coating composition that can satisfy the stringent requirements, as described above, for applying on at least one surface of a medical device and can be prepared through a process that is compatible with the pharmaceutical or therapeutic agents physically or chemically impregnated in the coatings.

SUMMARY OF THE INVENTION

Accordingly, the present invention provides a tri-branched copolymer comprising a hydrophobic domain, a hydrophilic domain, a biologically active moiety, and an alkyl core of 2 to 10 carbon atoms; the hydrophobic domain, the hydrophilic domain, and the biologically active moiety are separately linked to the alkyl core of 2 to 10 carbon atoms through three functional groups, wherein said three functional groups are the same or different, and are selected from a covalent bond, —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole, wherein R is hydrogen or C1-C6 alkyl.

Preferably, the tri-branched copolymer comprises the following structure:

(I)

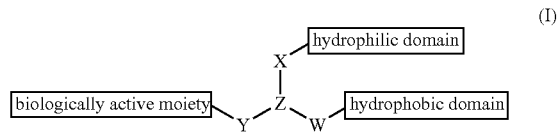

wherein Z is an alkyl group of 2 to 10 carbon atoms; X, Y, and W are the same or different, and are functional groups selected from a covalent bond, —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole, wherein R is hydrogen or C1-C6 alkyl.

In one embodiment of the present invention, the tri-branched copolymer comprises the following structure:

(II)

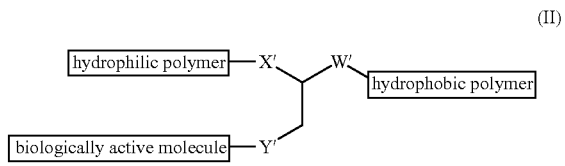

wherein X' and Y' are the same or different, and are functional groups selected from —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole; W' is a functional group selected from a covalent bond, —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole; and R is hydrogen or C1-C6 alkyl. Preferably, W' is a covalent bond.

In another embodiment of the present invention, the tri-branched copolymer comprises the following structure:

(III)

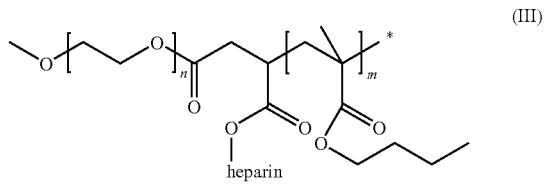

wherein n and m are the same or different, and are independently an integer of 10 to 2500.

The present invention also provides a coating composition for applying on at least a portion of one surface of an article, said coating composition comprising a tri-branched copolymer having a hydrophobic domain, a hydrophilic domain, a biologically active moiety, and an alkyl core of 2 to 10 carbon atoms; the hydrophobic domain, the hydrophilic domain, and the biologically active moiety are separately linked to the alkyl core of 2 to 10 carbon atoms through three functional groups, wherein said three functional groups are independently the same or different, and are selected from a covalent bond, —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole, wherein R is hydrogen or C1-C6 alkyl.

In another aspect, the present invention provides an article having a coating thereon, said coating comprising a tri-branched copolymer having a hydrophobic domain, a hydrophilic domain, a biologically active moiety, and an alkyl core of 2 to 10 carbon atoms; the hydrophobic domain, the hydrophilic domain, and the biologically active moiety are separately linked to the alkyl core of 2 to 10 carbon atoms through three functional groups, wherein said three functional groups are independently the same or different, and are selected from a covalent bond, —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole, wherein R is hydrogen or C1-C6 alkyl.

DETAILED DESCRIPTION OF THE INVENTION

The present invention provides a tri-branched copolymer comprising a hydrophobic domain, a hydrophilic domain, a biologically active moiety, and an alkyl core of 2 to 10 carbon atoms. By "tri-branched", it is meant that the inventive copolymer has a shape of "Y", wherein the alkyl core of 2 to 10 carbon atoms serves as a center core, and the hydrophobic domain, the hydrophilic domain, and the biologically active moiety are as three branches extending from the center core. That is, the three branches of the inventive copolymer are the hydrophobic domain, the hydrophilic domain, and the biologically active moiety, respectively. The term "domain" as used herein denotes a block of polymerized monomer units. The hydrophobic domain, the hydrophilic domain, and the biologically active moiety are separately linked to the alkyl core of 2 to 10 carbon atoms through three functional groups. The three functional groups are independently the same or different. Examples of the functional groups suitable for the present invention include, but are not limited to: a covalent bond, —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole; wherein R is hydrogen or C1-C6 alkyl. As used herein, "(CO)" denotes a carbonyl moiety; —(CNR)— denotes an imine moiety; "(SO)" denotes a sulfinyl moiety; and "(SO$_2$)" denotes a sulfonyl moiety. When one or more of the three functional groups are covalently bonds, the hydrophobic domain, the hydrophilic domain, and/or the biologically active moiety are directly attached to the alkyl core through the one or more covalent bonds, respectively.

Preferably, the tri-branched copolymer comprises the following structure:

(I)

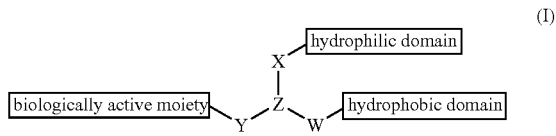

wherein Z is an alkyl group of 2 to 10 carbon atoms; X, Y, and W are the same or different, and are functional groups selected from the group consisting of a covalent bond, —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole, wherein R is hydrogen or C1-C6 alkyl.

The hydrophobic domain of the tri-branched copolymer comprises repeating monomer units of one or more alkyl methacrylate or alkyl acrylate. The hydrophilic domain of the tri-branched copolymer comprises repeating monomer units selected from acrylamide, N,N-dimethyl acrylamide, N-isopropyl acrylamide, acrylic acid, styrene sulfonic acid, vinyl alcohol, ethylene glycol, and N-vinyl pyrrolidone. By "alkyl methacrylate", it is meant a methacrylate derivative wherein the oxygen atom attached to the carbon atom of the carbonyl group is substituted with an alkyl group. By "alkyl acrylate", it is meant an acrylate derivative wherein the oxygen atom attached to the carbon atom of the carbonyl group is substituted with an alkyl group. Examples of alkyl methacrylate suitable for the present invention include, but are not limited to: methyl methacrylate, ethyl methacrylate, propyl methacrylate, butyl methacrylate, pentyl methacrylate, hexyl methacrylate, heptyl methacrylate, octyl methacrylate, nonyl methacrylate, and dodecyl methacrylate. Examples of alkyl acrylate suitable for the present invention include, but are not limited to: methyl acrylate, ethyl acrylate, propyl acrylate, butyl acrylate, pentyl acrylate, hexyl acrylate, heptyl acrylate, octyl acrylate, nonyl acrylate, and dodecyl acrylate.

The biologically active moiety of the tri-branched copolymer is derived from a biologically active molecule. Preferably, the biologically active moiety is adjacent to the hydrophilic domain. The "biologically active molecule" as used herein denotes a compound or substance having an effect on or eliciting a response from living tissue. The biologically active molecules suitable for the present invention include, for example, any drugs, agents, compounds and/or combination thereof that have therapeutic effects for treating or preventing a disease or a biological organism's reaction to the introduction of the medical device to the organism. Preferred biological active molecules include, but are not limited to: anti-thrombogenic agents, immuno-suppressants, anti-neoplastic agents, anti-inflammatory agents, angiogenesis inhibitors, protein kinase inhibitors, and other agents which may cure, reduce, or prevent restenosis in a mammal. The biological active molecules suitable for the present invention also include proteins, polypeptides, oligopeptides, DNA, RNA, siRNA, ribozymes, polysaccharides, oligosaccharides, lipids, lipoproteins, and proteoglycans. Examples of the biological active molecules of the present invention include, but are not limited to: heparin, albumin, streptokinase, tissue plasminogin activator (TPA), urokinase, rapamycin, paclitaxel, pimecrolimus, proteins, polypeptides, oligopeptides, DNA, RNA, siRNA, ribozymes, polysaccharides, oligosaccharides, lipids, lipoproteins, proteoglycans, and their analogs and derivatives. Preferably, the heparin used in the present invention is a low molecular weight heparin. The biologically active moiety imparts biological activity to the inventive copolymer. Since a wide range of biologically active molecules can be used for the biologically active moiety, the biological activity of the tri-branched copolymer may be adjusted accordingly.

In one embodiment of the present invention, the tri-branched copolymer comprises the following structure:

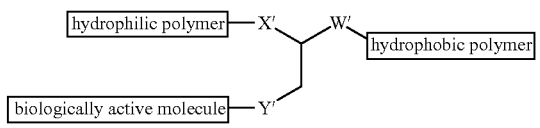

(II)

wherein X' and Y' are the same or different, and are functional groups selected from —(CO)—, —(CNR)—, —(SO)—, —(SO₂)—, —O(CO)—, —(CO)O—, —NH(CO)—, —(CO)NH—, —O(SO₂)—, —(SO₂)O—, —O(SO)—, —(SO)O—, —NH(SO₂)—, —(SO₂)NH—, —NH(SO)—, —(SO)NH—, and triazole; W' is a functional group selected from a covalent bond, —(CO)—, —(CNR)—, —(SO)—, —(SO₂)—, —O(CO)—, —(CO)O—, —NH(CO)—, —(CO)NH—, —O(SO₂)—, —(SO₂)O—, —O(SO)—, —(SO)O—, —NH(SO₂)—, —(SO₂)NH—, —NH(SO)—, —(SO)NH—, and triazole; and R is hydrogen or C1-C6 alkyl. Preferably, W' is a covalent bond.

In another embodiment of the present invention, the tri-branched copolymer comprises the following structure:

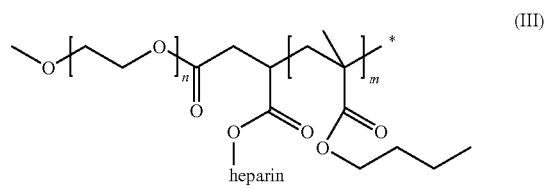

(III)

wherein n and m are the same or different, and are independently an integer of 10 to 2500.

The tri-branched copolymer may be prepared through living polymerization methods and conjugation reactions. More preferably, the tri-branched copolymer is prepared through reversible addition fragmentation transfer (RAFT) polymerization and conjugation reactions. To prepare the tri-branched copolymer, RAFT polymerization and conjugation reactions may be conducted in any sequence. Many conventional polymerization methods require chemical crosslinking reactions, high temperature curing processes, and/or plasma treatments, which not only have very limited control over the polymer molecular weight distribution, but also cause damages to the therapeutic agent impregnated in the coating and the drug-content in the underlying basecoat. Unlike those conventional polymerization methods, RAFT polymerization allows precise control of the molecular weight and molar ratio of each segment of a copolymer at ambient temperature, thereby providing a copolymer with predetermined molecular weight and narrow polydispersity, i.e., narrow molecular weight distribution. Thus, the structure and the molecular weight of the tri-branched copolymer may be precisely tuned through employment of RAFT polymerization.

Accordingly, the properties of the tri-branched copolymer may be tuned via adjusting the structure and/or the molar ratio of the hydrophobic domain and the hydrophilic domain. In other words, the structure and/or the molar ratio of the hydrophobic domain and the hydrophilic domain may be adjusted according to the desired properties of the tri-branched copolymer. For example, the hydrophilicity or hydrophobicity of the tri-branched copolymer may be adjusted through the use of hydrophilic domain and/or hydrophobic domain having different repeating monomer units, and/or through controlling the molar ratio between the hydrophobic domain and the hydrophilic domain. Furthermore, the hydrophobic domain and the hydrophilic domain need to be in a molar ratio that ensures desired mechanical strength of the tri-branched copolymer while providing a hydrophilic environment for retaining the optimal activity of the biologically active moiety. Preferably, the tri-branched copolymer has the hydrophobic domain and the hydrophilic domain in a mole ratio of 1:1 or above. More preferably, the tri-branched copolymer has the hydrophobic domain and the hydrophilic domain in a mole ratio of 2:1 or above.

It is preferable that the tri-branched copolymer has a tunable polymer molecular weight ranging from about 5K to about 500K Daltons to enable the formation of a coating with desirable mechanical durability and adequate adhesiveness. As used herein, 1K denotes 1,000. Since the mechanical durability of a coating improves upon increasing polymer molecular weight, it is especially preferable that the tri-branched copolymer has a high polymer molecular weight of 10K to 500K Daltons for use in coatings for certain medical devices (e.g., stents) which require expansion and deployment in vivo.

In one embodiment of the present invention, the tri-branched copolymer is synthesized through a route illustrated in Scheme 1. Specifically, a hydrophilic polymer is first conjugated to a RAFT core agent to form the hydrophilic domain. The RAFT core agent for preparing the inventive copolymer of formula (III) is maleic anhydride. Next, the hydrophobic domain is constructed via RAFT polymerization using DTBA. The biologically active moiety is then constructed via a conjugation reaction using DCC and NHS. As used herein, "DTBA" denotes dithiobenzoic acid; "DCC" denotes dicyclohexylcarbodiimide; and "NHS" denotes N-hydroxyl succinimide. In Scheme 1, the hydrophilic domain, the hydrophobic domain, and the biologically active moiety of the inventive copolymer of formula (III) are polyethylene glycol, butyl methacrylate, and heparin, respectively. RAFT polymerization has been reported in recent literatures and one skilled in the art would be able to readily ascertain details of RAFT polymerization conditions (see, for example, Shi, Peng-Jie; et al. European Polymer Journal, 2004, 40, 1283-1290).

wherein n and m are the same or different, and are independently an integer of 10 to 2500.

In another embodiment of the present invention, the tri-branched copolymer is synthesized through a route illustrated in Scheme 2. Specifically, a RAFT polymerization between a RAFT core agent of formula (IV) and a hydrophobic polymer is first conducted to construct the hydrophobic domain. Then, the hydrophilic domain and the biologically active moiety are constructed in any sequence or simultaneously through conjugation reactions with a hydrophilic polymer and a biologically active molecule, respectively.

Scheme 2:

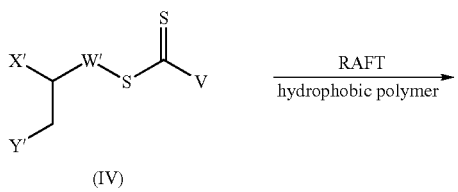

Scheme 1:

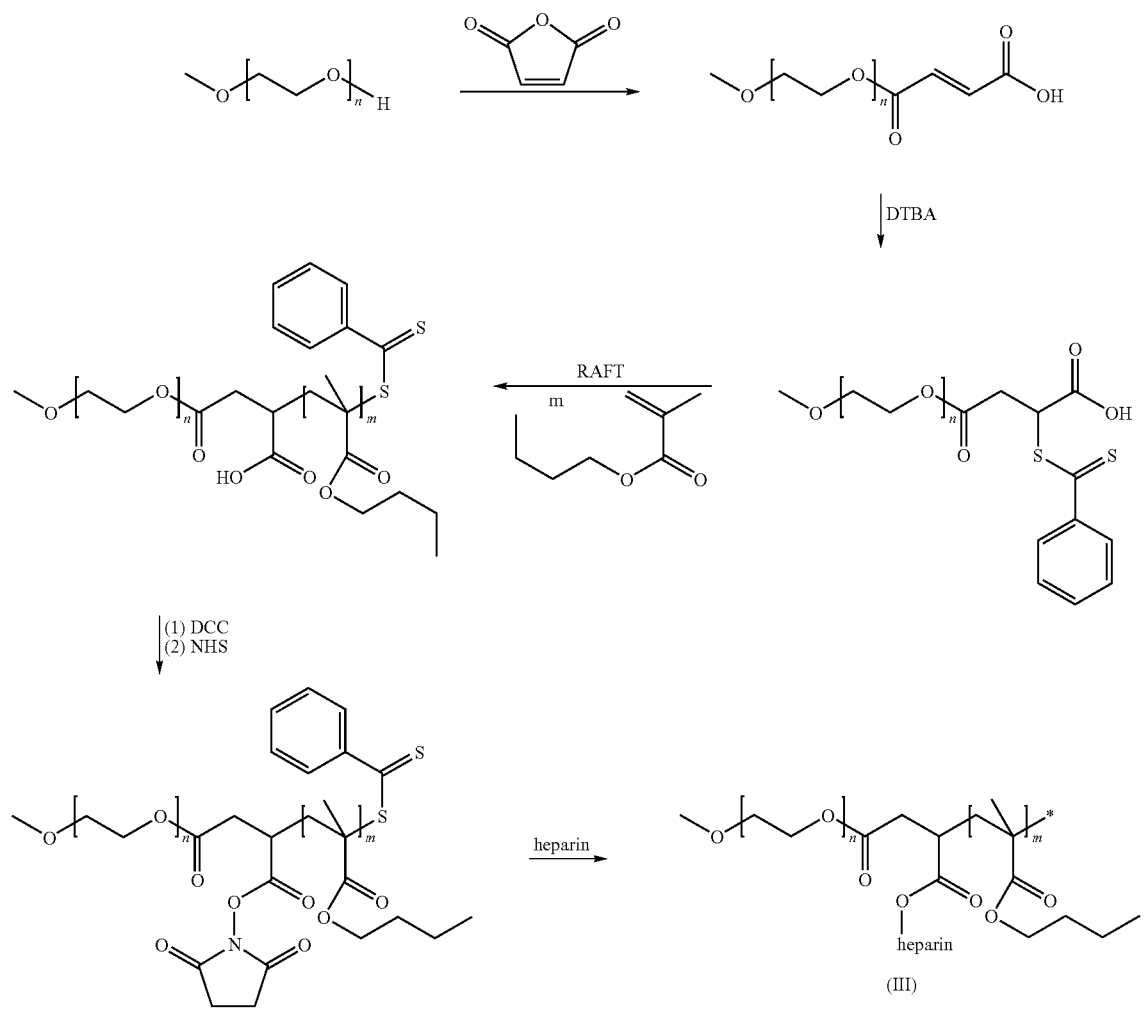

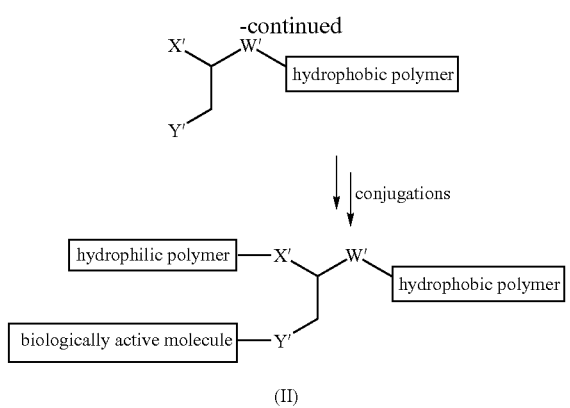

(II)

wherein X' and Y' are the same or different, and are functional groups selected from —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole; W' is a functional group selected from a covalent bond, —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole; R is hydrogen or C1-C6 alkyl; and V is an organic moiety suitable to be used as part of a RAFT agent. Preferably, V is phenyl. More preferably, V is phenyl and W' is a covalent bond.

RAFT polymerization and conjugation reactions enable efficient preparation of the tri-branched copolymer from readily available starting materials. As illustrated in Schemes 1 and 2, commercially available hydrophilic polymers and hydrophobic polymers may be directly used to construct the hydrophilic domain and the hydrophobic domain of the tri-branched copolymer. Furthermore, a commercially available RAFT core agent may provide the functional groups and the alkyl core of 2 to 10 carbon atoms of the tri-branched copolymer. Therefore, the tri-branched copolymer can be readily prepared avoiding complex synthetic processes for constructing the hydrophilic domain, the hydrophobic domain, the functional groups, and the alkyl core of 2 to 10 carbon atoms.

The present invention also provides a coating composition for applying on at least a portion of one surface of an article. The coating composition comprises a tri-branched copolymer having a hydrophobic domain, a hydrophilic domain, a biologically active moiety, and an alkyl core of 2 to 10 carbon atoms. The hydrophobic domain, the hydrophilic domain, and the biologically active moiety are separately linked to the alkyl core of 2 to 10 carbon atoms through three functional groups. The three functional groups are independently the same or different. Examples of the functional groups suitable for the present invention include, but are not limited to: a covalent bond, —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole; wherein R is hydrogen or C1-C6 alkyl.

The inventive coating composition may additionally include other polymers, co-solvents, and/or other additives to facilitate high quality film formation, such as plasticizers, antifoaming agents, anticrater agents, and coalescing solvents. Other suitable additives to the inventive coating composition include, but are not limited to: bioactive agents, antimicrobial agents, antithrombogenic agents, antibiotics, pigments, radiopacifiers and ion conductors. Details concerning the selection and amounts of such ingredients are known to those skilled in the art.

The inventive coating composition may be applied on at least a portion of one surface of an article. In some embodiments, the inventive coating is applied to all exposed surfaces of an article. The thickness of the inventive coating composition may vary depending on the process used in forming the coating as well as the intended use of the article. Typically, and for a medical device, the inventive coating is applied to a thickness from about 1 nanometer to about 10 micrometer, with a thickness from about 10 nanometer to about 10 micrometer being more typical. The tri-branched copolymer is soluble in common organic solvents, such as tetrahydrofuran (THF), acetone, chloroform, dichloromethane, acetonitrile, dimethylformide (DMF), and mixtures thereof. Since organic solvents are widely used to handle polymeric material, the inventive coating composition may be applied on at least one surface of an article through various coating processes (e.g., spray coating process).

When applied on at least one surface of an article, the hydrophobic domain provides the tri-branched copolymer with improved mechanical durability and enhanced adhesion to the underlying surface, while the hydrophilic domain and the biologically active moiety impart lubricity and hemocompatibility. Furthermore, the hydrophobic domain and the hydrophilic domain are adjustable to obtain the desirable elasticity of the tri-branched copolymer. Moreover, the hydrophilic domain can hydrate and swell under physiological conditions and provide a desirable environment for the biologically active moiety to retain the biological activity.

The inventive coating composition may also be applied to control the elution of a therapeutic dosage of a pharmaceutical agent from a medical device base coating, for example, a stent base coating. The basecoat generally comprises a matrix of one or more drugs, agents, and/or compounds and a biocompatible material such as a polymer. The control over elution results from either a physical barrier, or a chemical barrier, or a combination thereof. The elution is controlled by varying the thickness of the coating, thereby changing the diffusion path length for the drugs, agents, and/or compounds to diffuse out of the basecoat matrix. Essentially, the drugs, agents and/or compounds in the basecoat matrix diffuse through the interstitial spaces in the coating. Accordingly, the thicker the coating, the longer the diffusion path, and conversely, the thinner the coating, the shorter the diffusion path. The effectiveness of the inventive coating composition as a regulator for drug elution from the basecoat may be maximized via tuning the relative molar ratio of the hydrophobic domain and the hydrophilic domain in the tri-branched copolymer for the optimal hydrophobicity of the tri-branched copolymer. It is important to note that both the basecoat and the coating thickness may be limited by the desired overall profile of the article on which they are applied.

The present invention also provides an article having a coating composition thereon. The coating composition comprises a tri-branched copolymer having a hydrophobic domain, a hydrophilic domain, a biologically active moiety, and an alkyl core of 2 to 10 carbon atoms. The hydrophobic domain, the hydrophilic domain, and the biologically active moiety are separately linked to the alkyl core of 2 to 10 carbon atoms through three functional groups, wherein said three functional groups are independently the same or different. Examples of the functional groups suitable for the present invention include, but are not limited to: a covalent bond, —(CO)—, —(CNR)—, —(SO)—, —(SO$_2$)—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole; wherein R is hydrogen or C1-C6 alkyl. The at least a portion of one surface of the article may be a surface of a polymeric coat, a plastic substance, ceramic, steel, or other alloy metals.

The article that may be coated with the inventive coating composition may be in any shape, and is preferably a medical device or a component of a medical device. More preferably, the medical device or the component of a medical device is implantable. The term "medical device" as used herein denotes a physical item used in medical treatment, which includes both external medical devices and implantable medical devices. The medical devices that may be coated with the inventive coating composition include, but are not limited to: catheters, guidewires, drug eluting stents, cochlear implants, retinal implants, gastric bands, neurostimulation devices, muscular stimulation devices, implantable drug delivery devices, intraocular devices, and various other medical devices.

The present coating composition may be applied to the surface of an article using conventional coating techniques, such as, for example, spray coating, ultrasonic coating, dip coating, and the like. In a dip coating process, the article is immersed in a bath containing the coating composition and then removed. A dwelling time ranging from about 1 minute to about 2 hours may be used depending of the material of construction, complexity of the device, and the desired coating thickness. Next, the article coated with the coating composition may be allowed to dry to provide a dry coating. Drying may be accomplished merely by standing at ambient conditions or may be accelerated by heating at mild temperatures, such as about 30° C. to about 65° C.

While the present invention has been particularly shown and described with respect to preferred embodiments thereof, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

Having thus described the invention in detail, what is claimed as new and is desired to be secured by the Letters Patent is:

1. A tri-branched copolymer comprising the following structure:

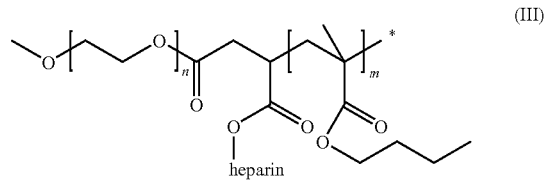

(III)

heparin wherein n and m are the same or different, and are independently an integer of 10 to 2500 and has a tunable molecular weight ranging from about 5K to about 500K Daltons.

2. A coating composition for applying on at least a portion of one surface of an article, said coating composition comprising the tri-branched copolymer of claim 1.

3. The coating composition of claim 2, wherein the coating has a thickness of about 1 nanometer to about 10 micrometer.

4. An article having a coating thereon, said coating comprising the tri-branched copolymer of claim 1.

5. The article of claim 4, wherein the coating has a thickness of about 1 nanometer to about 10 micrometer.

6. The article of claim 4 is a medical device or a component of a medical device.

* * * * *